(12) United States Patent
Sullivan et al.

(10) Patent No.: US 6,775,051 B2
(45) Date of Patent: Aug. 10, 2004

(54) SYSTEMS AND METHODS FOR SCANNING A BEAM OF LIGHT ACROSS A SPECIMEN

(75) Inventors: Jamie Sullivan, Sunnyvale, CA (US); Ralph Johnson, Los Gatos, CA (US); John Gibson, Sunnyvale, CA (US); Mingguang Li, Sunnyvale, CA (US); Eric Vella, Mt. View, CA (US)

(73) Assignee: KLA-Tencor Technologies, Milpitas, CA (US)

( * ) Notice: Subject to any disclaimer, the term of this patent is extended or adjusted under 35 U.S.C. 154(b) by 270 days.

(21) Appl. No.: 10/138,782

(22) Filed: May 3, 2002

(65) Prior Publication Data

US 2002/0181119 A1 Dec. 5, 2002

Related U.S. Application Data

(60) Provisional application No. 60/288,632, filed on May 3, 2001.

(51) Int. Cl.⁷ .............................. G02F 1/33; G11B 7/00; G11B 3/74
(52) U.S. Cl. ................. 359/312; 359/305; 359/308; 359/286; 369/116; 369/97; 369/121
(58) Field of Search .................. 359/312, 305, 359/308, 286; 369/116, 97, 121

(56) References Cited

U.S. PATENT DOCUMENTS

| 4,827,125 A | * | 5/1989 | Goldstein | ............ 250/234 |
|---|---|---|---|---|
| 5,321,683 A | | 6/1994 | Olczak | ............ 369/112.24 |
| 5,355,252 A | | 10/1994 | Haraguchi | ............ 359/369 |
| 5,633,747 A | * | 5/1997 | Nikoonahad | ............ 359/312 |
| 5,635,883 A | | 6/1997 | Penunuri et al. | ............ 333/195 |
| 5,864,394 A | * | 1/1999 | Jordan et al. | ............ 356/237.2 |

OTHER PUBLICATIONS

International Search Report, Application No. PCT/US02/14132, mailed Oct. 18, 2002.

* cited by examiner

*Primary Examiner*—Tim Thompson
(74) *Attorney, Agent, or Firm*—Ann Marie Mewherter; Conley Rose P.C.

(57) ABSTRACT

Systems and methods for scanning a beam of light over a specimen are provided. A system may include a pre-scan acousto-optical deflector (AOD) configured to deflect a beam of light, a second AOD configured as a traveling lens to focus the scanning beam, a relay lens, and an objective lens. The relay lens may be centered on the scan line produced by the second AOD, while the objective lens may be substantially de-centered with respect to the relay lens to produce a telecentric scanning spot with no field tilt. The system may modulate the amplitude of the sound wave in the first AOD to compensate for attenuation in the second AOD. The system may pre-fill one chirp packet in the second AOD while another chirp packet is scanning to substantially reduce a delay between consecutive scans.

42 Claims, 5 Drawing Sheets

SYSTEMS AND METHODS FOR SCANNING A BEAM OF LIGHT ACROSS A SPECIMEN

PRIORITY CLAIM

This application claims priority to U.S. Provisional Application No. 60/288,632 entitled "Systems and Methods for Scanning a Beam of Light Across a Specimen," filed May 3, 2001.

BACKGROUND OF THE INVENTION

1. Field of the Invention

This invention generally relates to systems and methods for scanning a beam of light across a specimen. Certain embodiments relate to systems and methods that may include acousto-optical deflectors configured to deflect a beam of light at various angles.

2. Description of the Related Art

Fabricating semiconductor devices such as logic and memory devices may typically include processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes may include, but are not limited to, chemical-mechanical polishing, etch, deposition, and ion implantation. Multiple semiconductor devices may be fabricated in an arrangement on a semiconductor wafer and then separated into individual semiconductor devices.

During each semiconductor device fabrication process, defects such as particulate contamination and pattern defects may be introduced into the semiconductor devices. Such defects may be isolated to a single semiconductor device on a semiconductor wafer containing several hundred semiconductor devices. For example, isolated defects may be caused by random events such as an unexpected increase in particulate contamination in a manufacturing environment or an unexpected increase in contamination in process chemicals which may be used in fabrication of the semiconductor devices. Alternatively, the defects may be repeated in each semiconductor device formed across an entire semiconductor wafer. In an example, repeated defects may be systematically caused by contamination or defects on a reticle. A reticle, or a mask, may be disposed above a semiconductor wafer and may have substantially transparent regions and substantially opaque regions that are arranged in a pattern that may be transferred to a resist. Therefore, contamination or defects on a reticle may also be reproduced in the pattern transferred to the resist and may undesirably affect the features of each semiconductor device formed across an entire semiconductor wafer in subsequent processing.

Defects on semiconductor wafers may typically be monitored manually by visual inspection, particularly in the lithography process because many defects generated during a lithography process may be visible to the naked eye. Such defects may include macro defects which may be caused by faulty processes during this step. Defects which may be visible to the human eye typically have a lateral dimension greater than or equal to approximately 100 µm. Defects having a lateral dimension as small as approximately 10 µm, however, may also be visible on unpatterned regions of a semiconductor wafer. Prior to the commercial availability of automated defect inspection systems such as the systems illustrated in U.S. Pat. Nos. 5,917,588 to Addiego and 6,020,957 to Rosengaus et al., which are incorporated by reference as if fully set forth herein, manual inspection was the most common, and may still be the most dominant, inspection method used by lithography engineers.

A method for manual inspection of a semiconductor wafer may involve placing the semiconductor wafer on a semiautomatic tilt table and rotating the wafer through various angles under a bright light. The semiautomatic tilt table may rotate the semiconductor wafer about a central axis while positioning the semiconductor wafer at different inclinations relative to a plane normal to the central axis. In this manner, an operator may visually inspect the semiconductor wafer for defects as it rotates. The operator may then determine if the defects present on the semiconductor wafer are within an acceptable limit of defects on the semiconductor wafer. An example of a visual inspection method is illustrated in U.S. Pat. No. 5,096,291 to Scott and is incorporated by reference as if fully set forth herein.

Automated inspection systems were developed to decrease the time required to inspect a wafer surface. Such inspection systems may typically include two major components such as an illumination system and a collection-detection system. An illumination system may include a light source such as a laser that may produce a beam of light and an apparatus for focusing and scanning the beam of light. Defects present on the surface may scatter the incident light. A detection system may detect the scattered light and may convert the detected light into electrical signals that may be measured, counted, and displayed on an oscilloscope or other monitor. The detected signals may be analyzed by a computer program to locate and identify defects on the wafer. Examples of such inspection systems are illustrated in U.S. Pat. Nos. 4,391,524 to Steigmeier et al., 4,441,124 to Heebner et al., 4,614,427 to Koizumi et al., 4,889,998 to Hayano et al., and 5,317,380 to Allemand, all of which are incorporated by reference as if fully set forth herein.

Acousto-optical deflection may generally be described as a technique for altering a path of a beam of light that typically involves propagating sound waves through a solid material. Sound waves propagating through the solid material may alter a property such as a refractive index of the solid material. As a result, a beam of light passing through the solid material may be deflected at various angles by the solid material due to the sound waves propagating through the material. In technical applications, acousto-optical deflectors ("AODs"), which may also be commonly referred to as acousto-optical scanners, in conjunction with focusing optics, may be used to scan a focused spot of light across a surface of a specimen. Such a technical application may include, for example, inspection of a specimen such as a semiconductor wafer.

An example of a system that includes an AOD is illustrated in U.S. Pat. No. 4,912,487 to Porter et al., which is incorporated by reference as if fully set forth herein. The system includes an argon ion laser beam that may illuminate a specimen surface. An acousto-optical deflector is driven with a chirp signal and placed in the path of the beam to cause it to sweep out raster scan lines. The target is placed on an XY translation stage capable of bi-directional movement. The beam has an angle of incidence normal to the target and the stage moves so that it is scanned along adjacent contiguous strips of equal width. Additional examples of systems that may include AODs are illustrated in U.S. Pat. Nos. 5,633,747 to Nikoonahad, 5,833,710 to Nikoonahad et al., 5,864,394 to Jordan, III et al., and 6,081,325 to Leslie et al., which are incorporated by reference as if fully set forth herein.

SUMMARY OF THE INVENTION

Increasing demands for higher throughput and lower cost requirements in semiconductor device manufacturing overall translates into a need for processing and inspection systems having higher accuracy and speed than currently available systems. Such inspection systems may include an AOD. Leading edge AOD scanning inspection systems may include an AOD having a high bandwidth and long acoustic propagation time to provide substantially higher throughput systems with substantially simpler XY translation stages. In addition, such a system may be required to produce substantially uniform spot sizes and substantially uniform brightness across a scan line for substantially constant sensitivity throughout the scan. If a sensitivity of such a system is not consistent across the scan line, system-to-system matching as in multiple machine system applications and environments may be problematic. In addition, producing substantially constant spot sizes across larger scan lengths may improve a data acquisition rate of a system because a larger portion of a specimen may be scanned in a single scan. In this manner, a throughput of such a system may also be increased.

In an embodiment, a system may be configured to scan a focused spot of light over a surface of a specimen. The system may include an AOD and optics configured to focus a beam of light to a small spot and to scan this spot across a line considerably longer than the size of the spot. The AOD may be operated in "deflection mode," in which the entire AOD is filled with a nearly constant frequency sound wave, which deflects the beam at a nearly constant angle. In this mode, a scan line may be produced by varying the AOD frequency as a function of time. Alternatively, the AOD may be operated in "chirp mode," in which a portion of the AOD is filled with a sound wave with rapidly varying frequency ("chirp packet"), which focuses the beam to a small spot. In this mode, a scan line may be produced by the propagation of the chirp packet across the length of the AOD.

The system may also include a relay lens. The relay lens may be configured to collimate the light from a scan line produced by an AOD operated in chirp mode. The optical axis of the relay lens may be substantially centered on the scan line produced by the AOD. The optical axis of the relay lens may also be substantially perpendicular to the scan line produced by the AOD but not parallel to the chief ray produced by the AOD. In addition, the system may include an objective lens. The optical axis of the objective lens may be substantially parallel to but substantially de-centered with respect to the optical axis of the relay lens. The collimated light, however, may be substantially centered on the objective lens.

The system may also include a prism or mirror assembly located between the relay lens and an objective lens. The prism or mirror assembly may be configured to re-center the collimated light onto the objective lens to avoid the need to de-center the objective lens from the axis of the relay lens.

The objective lens may be configured to focus the collimated light to a focal plane. The objective lens may be oriented substantially parallel to the focal plane. In addition, the optical axis of the objective lens may be substantially centered on and perpendicular to the focal plane. The focal plane may be substantially parallel to the surface of the specimen. Therefore, such a system may reduce, and may even substantially eliminate, field tilt of the system. Field tilt may be generally described as an angle at which a focal plane of a system may be located with respect to a surface of a specimen. Such field tilt may result, for example, from using an AOD in chirp mode with centered relay optics.

Field tilt may not be problematic for field sizes that are not large relative to the spot size of light within the field. Relatively small field sizes, however, may have several disadvantages. For example, a system that may have a relatively small field size may have a relatively low throughput and may require a complex, high performance XY translation stage in comparison to a system that may have a relatively large field size. As field size increases, however, field tilt may reduce spot size uniformity across the field. For example, spot sizes further from the center of the field may become larger and defocused due to tilt of the focal plane. For systems with field tilt, the amount of defocus scales as the square of the distance from the center of the scan line. In this manner, sensitivity of such a system may also vary across the field. In addition, if the sensitivity of the system varies, then the performance of a plurality of such systems may vary from system-to-system. Therefore, field tilt may become more problematic in leading edge inspection systems.

Because field tilt of a system as described herein may be reduced, and even substantially eliminated, the spot size of a beam of light on the surface of the specimen may be substantially independent of a position of the beam of light on the surface of the specimen. Therefore, such a system may have a relatively large field size. Consequently, the system may also have a relatively high throughput and a simple and relatively inexpensive XY translation stage. In addition, spots throughout substantially the entire field of such a system may have a substantially constant size and focus. Therefore, the sensitivity of the system may be substantially independent of the position of the beam of light on the surface of the specimen. In this manner, because the sensitivity of the system may be substantially uniform, performance of a plurality of such systems may be substantially uniform from system-to-system, thereby enabling improved system-to-system matching.

In an embodiment, a system may be configured to scan a beam of light over a surface of a specimen. The system may include a first AOD and a second AOD. The first AOD may be configured to direct the beam of light at various angles through an optical system onto the second AOD. The brightness of the beam produced by the first AOD may be calibrated with a substantially uniform scattering feature.

The first AOD may be operated in deflection mode, where the drive signal duration is longer than the propagation time of an acoustic wave across the light beam. The system may also include a lens configured to expand the beam created by the first AOD and convert the angular scan into a substantially parallel scan. The second AOD may be operated in chirp mode, where the drive signal duration is approximately equal to the propagation time of the acoustic wave across the beam. The second AOD may be configured to function as a traveling lens to focus the scanning beam. The length of a chirp packet traveling in the second AOD may be much smaller than the length of the second AOD. In this manner, light directed by the second AOD may scan a surface of a specimen.

The amplitude of the drive signal applied to the first AOD may be modulated to control the brightness of the deflected beam. This intensity modulation may be used to compensate for transmission losses over the length of the second AOD or over the entire inspection system. "Transmission loss" of an AOD may generally describe changes in the intensity of the light deflected by the AOD. The transmission loss is caused by attenuation of the acoustic chirp packet as the chirp packet propagates through the solid medium of the AOD. A "chirp packet" may generally refer to an acoustic wave propagating through an AOD produced by an excitation such as a radio-frequency signal from a generator coupled to the AOD through a transducer. Transmission losses may cause changes in intensity of light deflected by the AOD over a length of the AOD. In addition, an intensity of the deflected light may become less uniform as a length of an AOD increases.

In an embodiment, the amplitude of a drive signal applied to the first AOD may be modulated such that an intensity of the light over the scan line of the first AOD may increase as transmission losses over a length of the second AOD increase. Therefore, such a system may compensate for acoustical attenuation over the length of the second AOD. This mechanism may also be used to compensate for other losses in the optical system. In this manner, an intensity of the light directed by the second AOD may be substantially independent of a position of the directed beam of light on the surface of the specimen. As such, a sensitivity of the system may be substantially independent of a position of the directed beam of light on the surface of the specimen. Therefore, as described above, a performance of a plurality of such systems may be substantially uniform from system-to-system, thereby enabling system-to-system matching.

In an additional embodiment, a system may be configured to scan a beam of light over a surface of a specimen. The system may include an AOD operating in chirp mode. The AOD may include more than one chirp packet at the same time. While a first chirp packet is propagating through the AOD and is illuminated to form a scan line, a second chirp packet may be prepared to begin a subsequent scan line. This arrangement, called "prefilling," may eliminate the lost time associated with filling the chirp packet at the beginning of each scan line.

In addition, the system may include a field stop. The field stop may be configured to allow only one chirp packet at a time to scan the specimen. For example, while the first chirp packet is scanning the specimen, the field stop may block light deflected from the second chirp packet; conversely, when the second chirp packet is fully prepared and begins scanning the specimen, the field stop then blocks light from the first chirp packet.

An average data rate of such a system may be approximately equal to a peak data rate of the system. By pre-filling the AOD in this manner, the time required to fill an acoustic cell may be substantially eliminated from the process time of the system. In addition, such a system may substantially continuously scan light over a surface of a specimen. For example, a process time of such a system may include only a time required to scan the specimen, a fill time of a prescanner AOD, and a reset time of the electronics. As such, a data rate of such a system may only be limited by a fill time of the pre-scanner and a reset time of the electronics. In addition, because a throughput of such a system may depend on the data rate of the system, a throughput of such a system may also be increased.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
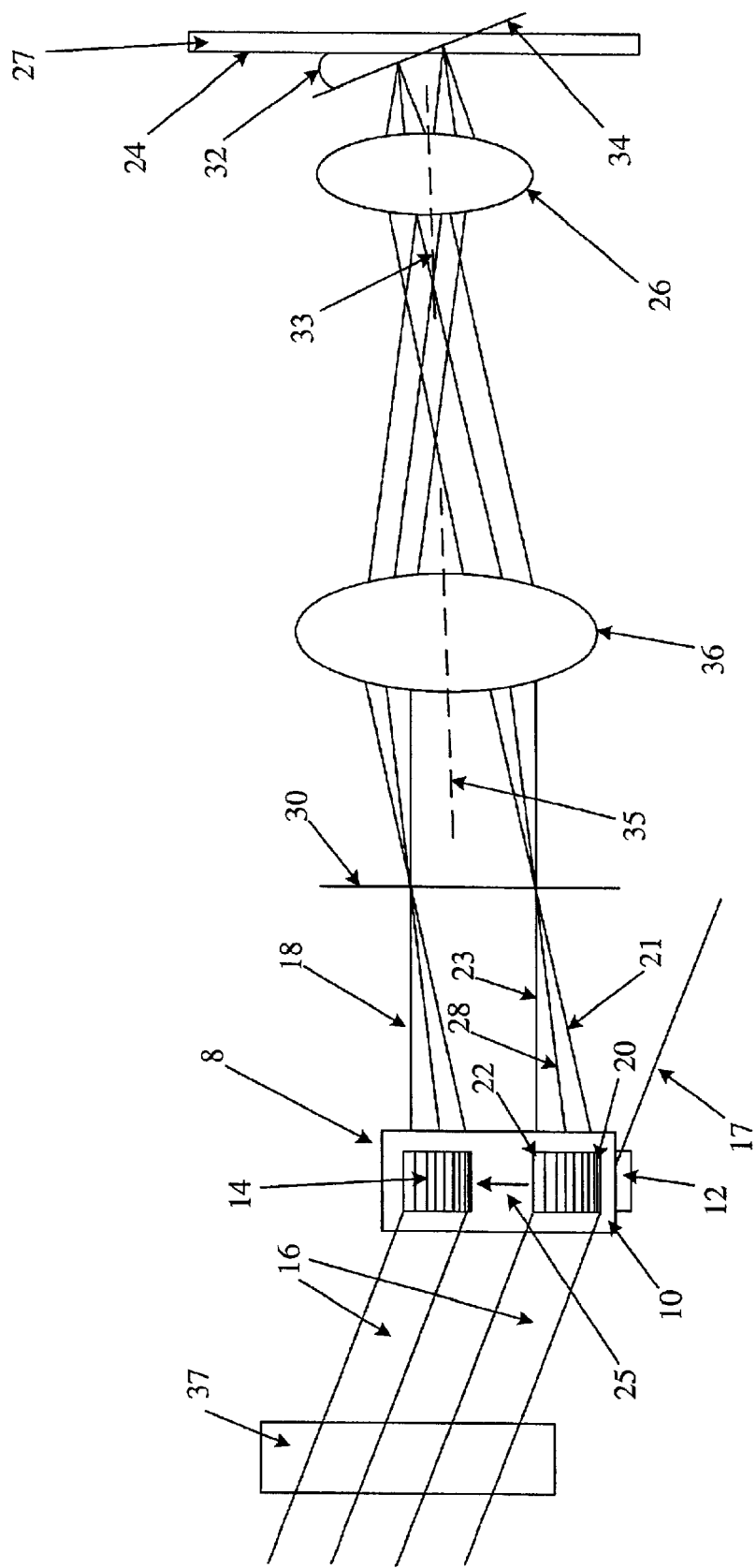
FIG. 1 depicts a schematic of an embodiment of a system that includes a relay lens that is substantially centered on an objective lens.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, FIG. 1 illustrates an embodiment of a system configured to scan a beam of light over a surface of a specimen. The system may include AOD 8. The system may also include a light source (not shown) configured to direct light 16 to AOD 8. For example, an appropriate light source may include, but may not be limited to, a helium neon laser, an argon ion laser, a solid state laser diode, a xenon arc lamp, an incandescent lamp, a light emitting diode, a fiber optic light source, or any other light source known in the art. In this manner, light 16 may include monochromatic light or light of multiple wavelengths. A single wavelength or multiple wavelengths of light 16 may include light of ultraviolet, visible, and/or infra-red wavelengths.

AOD 8 may be made of solid medium 10. Solid medium 10 may include, but is not limited to, a crystal material such as $TeO_2$, quartz, fused silica, sapphire, another glassy material, or any other appropriate material known in the art. Sound transducer 12 may be coupled to a surface of solid medium 10. Transducer 12 may be configured to initiate propagation of chirp packet 14 through solid medium 10. For example, a signal generator (not shown) may be configured to generate and provide a radio-frequency signal to transducer 12. Such a signal may be commonly referred to as a "drive signal." The wavelength of the sound wave may depend on the frequency of the drive signal and the velocity of sound in solid medium 10. In addition, the drive signal duration may be less than the transit time of a chirp packet traveling through solid medium 10. Therefore, as shown in FIG. 1, multiple sound waves chirp packets 14 may be propagating through AOD 8 at substantially the same time. As described above, such an AOD drive configuration may be commonly referred to as a "chirp mode."

Chirp packet 14 propagating through solid medium 10 may have a frequency in the ultrasonic range. Chirp packet 14 propagating through solid medium 10 may alter a property of solid medium 10 such as a lattice structure of the crystal or a refractive index. In this manner, light beam 16 incident on solid medium 10 may propagate through the solid medium and may be diffracted by a portion of the crystal lattice altered by the ultrasonic chirp packet as it propagates through the crystal. As a result, a portion of light 16 exiting solid medium 10 may include deflected beam 18. A portion of light 16 exiting solid medium 10, however, may also include substantially undeflected beam 17. Chirp packet 14 may contain multiple frequencies that change linearly from the start of the packet to the end of the chirp packet commonly referred to as a "frequency ramp."

An angle at which beam 18 may be deflected may depend only upon relative wavelengths of light and ultrasound waves inside solid medium 10. In this manner, an angle of deflection of a beam exiting solid medium 10 may be determined and may be controlled by a wavelength of light incident upon solid medium 10 and a wavelength of an ultrasonic sound wave induced inside solid medium 10. For the case of the chirp mode where the drive frequency changes linearly over chirp packet 14, the incident beam 16 is diffracted at different angles proportional to the frequency in the chirp packet. By ramping the frequencies from low to high, portion 20 of chirp packet 14 may have a higher frequency than portion 22. Because portion 20 has a higher frequency, it diffracts a portion of incident light beam 16 through a steeper angle as shown by diffracted beam 21. Because portion 22 has a relatively lower frequency, it diffracts a portion of incident light beam 16 through a more shallow angle as shown by diffracted light beam 23. In this manner, chirp packet 14 can be used to focus beam 16 in the plane shown as scan line 30. As chirp packet 14 propagates through medium 10, it acts as a traveling cylinder lens. Additional cylinder lens 37 can be used to focus beam 16 in the opposite plane. A light source and optical system (not shown) can be configured to sweep light beam 16 to track or follow chirp packet 14 as it propagates from transducer 12 through medium 10 along vector direction 25. In this manner, a scanning spot is generated at scan line 30.

An AOD configured in a chirp mode, as defined above, may be restricted to having a bandwidth, or a range of frequencies, of less than approximately 1 octave. Such bandwidth limitations may minimize, or may substantially eliminate, secondary beams of light deflected by the AOD from scanning the surface of a specimen at the same time as the primary beam of light deflected by the AOD. Such an AOD configuration, however, will produce a chief ray 28 that will not be perpendicular to scan line 30 generated by AOD 8.

As shown in FIG. 1, the system may also include an optical system for relaying the scanning spot located at scan line 30 to surface 24 of specimen 27. This system may include relay lens 36. Relay lens 36 may be configured to collimate light focused by AOD 8 and cylinder lens 37. Relay lens 36 may include any appropriate lens known in the art. Optical axis 35 of relay lens 36 may be centered on scan line 30 produced by AOD 8. Optical axis 35 may be parallel to the chief ray 28 of AOD 8. The system may also include objective lens 26. Objective lens 26 may be configured to focus the light collimated by relay lens 36 to focal plane 34. Objective lens 26 may include any focusing lens known in the art. As shown in FIG. 1, optical axis 33 of objective lens 26 may be coincident with optical axis 35 of relay lens 36. In such an arrangement, objective lens 26 may not be parallel to focal plane 34. For example, focal plane 34 may be located at angle 32 with respect to surface 24 of specimen 27. As described above, angle 32 at which the focal plane may be orientated with respect to the surface of the specimen may be commonly referred to as "field tilt." If a focal plane of a system is not substantially parallel to a surface of a specimen, a size of the beam of light (spot size) on surface 24 of specimen 27 may change across the surface. In addition, the sensitivity of the system may change across surface 34 due to changes in the brightness of light across surface 34.

Figure 2:
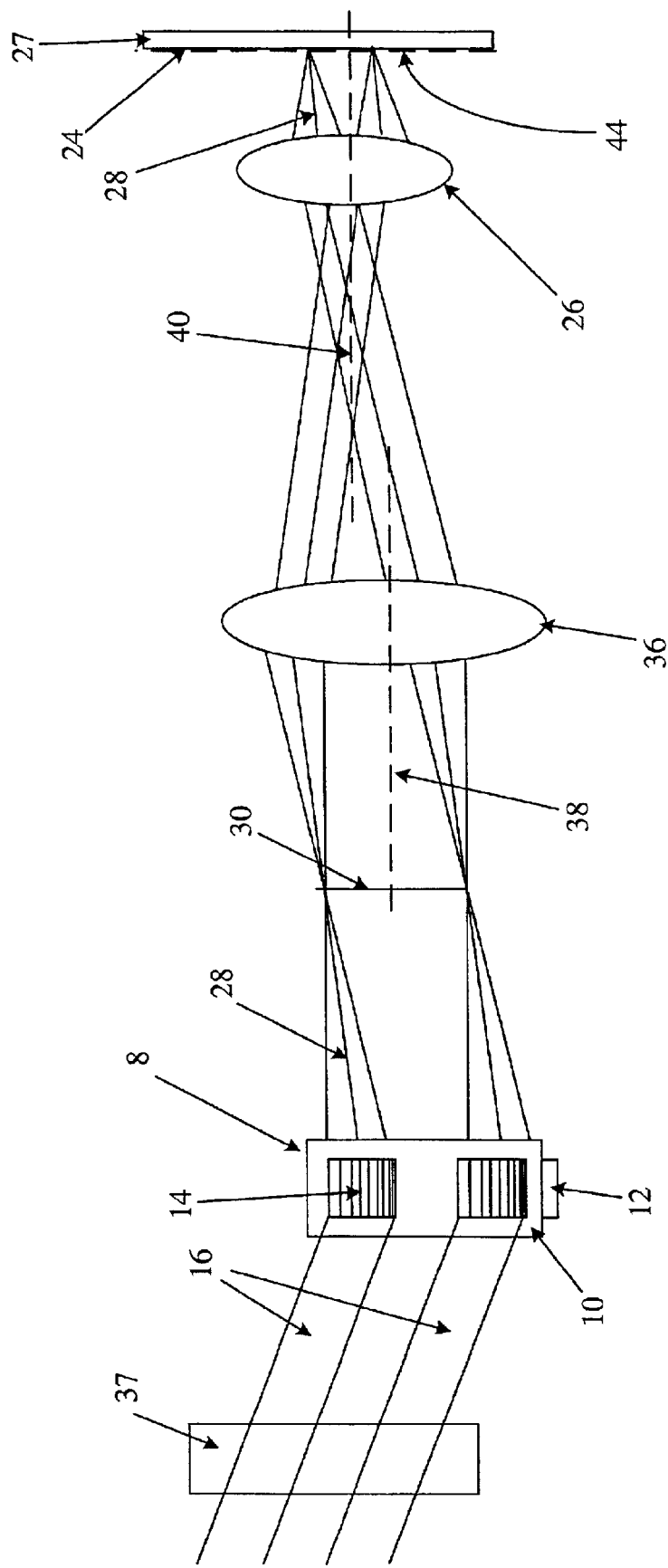
FIG. 2 depicts a schematic of an embodiment of a system that includes a relay lens that is substantially de-centered from an objective lens.

FIG. 2 illustrates a preferred embodiment of a system in which the optical axis of relay lens is centered on the scan line produced by the AOD operated in the chirp mode, but the optical axis of relay lens and objective lens are not parallel to the chief ray produced by the AOD operated in chirp mode. In addition the relay lens is substantially de-centered with respect to an objective lens. This system differs from the system depicted in FIG. 1 by producing a telecentric scanning spot without field tilt.

The system may include AOD 8. AOD 8 may be configured as in any of the embodiments described herein. For example, AOD 8 may be configured such that a drive signal provided to AOD 8 by transducer 12 may propagate chirp packet 14 through solid medium 10 of the AOD. Light 16 may be directed to AOD 8 from a light source (not shown). The light source may be configured as in any of the embodiments described herein. Light 16 deflected by AOD 8 at various angles may be focused to scan line 30 as described herein. In addition, the system may include relay lens 36. Relay lens 36 may be configured to collimate light deflected and focused by AOD 8 and cylinder lens 37. As shown in FIG. 2, optical axis 38 of relay lens 36 may be centered on scan line 30 produced by AOD 8. In addition, optical axis 38 of relay lens 36 may be perpendicular to scan line 30 produced by AOD 8. Optical axis 38 of relay lens 36 may not be substantially parallel to chief ray 28 produced by AOD 8.

The system may also include objective lens 26. Objective lens 26 may be configured to focus the light collimated by relay lens 36 to focal plane 44. Optical axis 40 of objective lens 26 may be substantially de-centered with respect to optical axis 38 of relay lens 36. Optical axis 40 of objective lens 26 may be substantially parallel to optical axis 38 of relay lens 36. The pupil of the light collimated and formed by relay lens 36, however, may be substantially centered on objective lens 26. In addition, objective lens 26 may be substantially parallel to focal plane 44. In this manner, objective lens 26 may be substantially centered on focal plane 44. As such, chief ray 28 deflected by AOD 8 may be relayed by this optical system at a substantially perpendicular angle to focal plane 44, as shown in FIG. 2. Furthermore, focal plane 44 may be substantially parallel to surface 24 of specimen 27. In this manner, an angle at which the focal plane may be located with respect to the surface of the specimen may be approximately 0 degrees. Therefore, field tilt associated with a chirp mode of an AOD may be corrected by a system in which the optical axis of an objective lens may be offset from the optical axis of a relay lens.

The system, as shown in FIG. 2, may also include additional optical components (not shown). For example, additional optical components may include, but may not be limited to, beam splitters, quarter wave plates, polarizers such as linear and circular polarizers, rotating polarizers, rotating analyzers, collimators, focusing lenses, mirrors, dichroic mirrors, partially transmissive mirrors, filters such as spectral or polarizing filters, spatial filters, reflectors, and modulators. Each of these additional optical components may be disposed within the system or may be coupled to any of the components of the system as described herein.

Figure 2A:
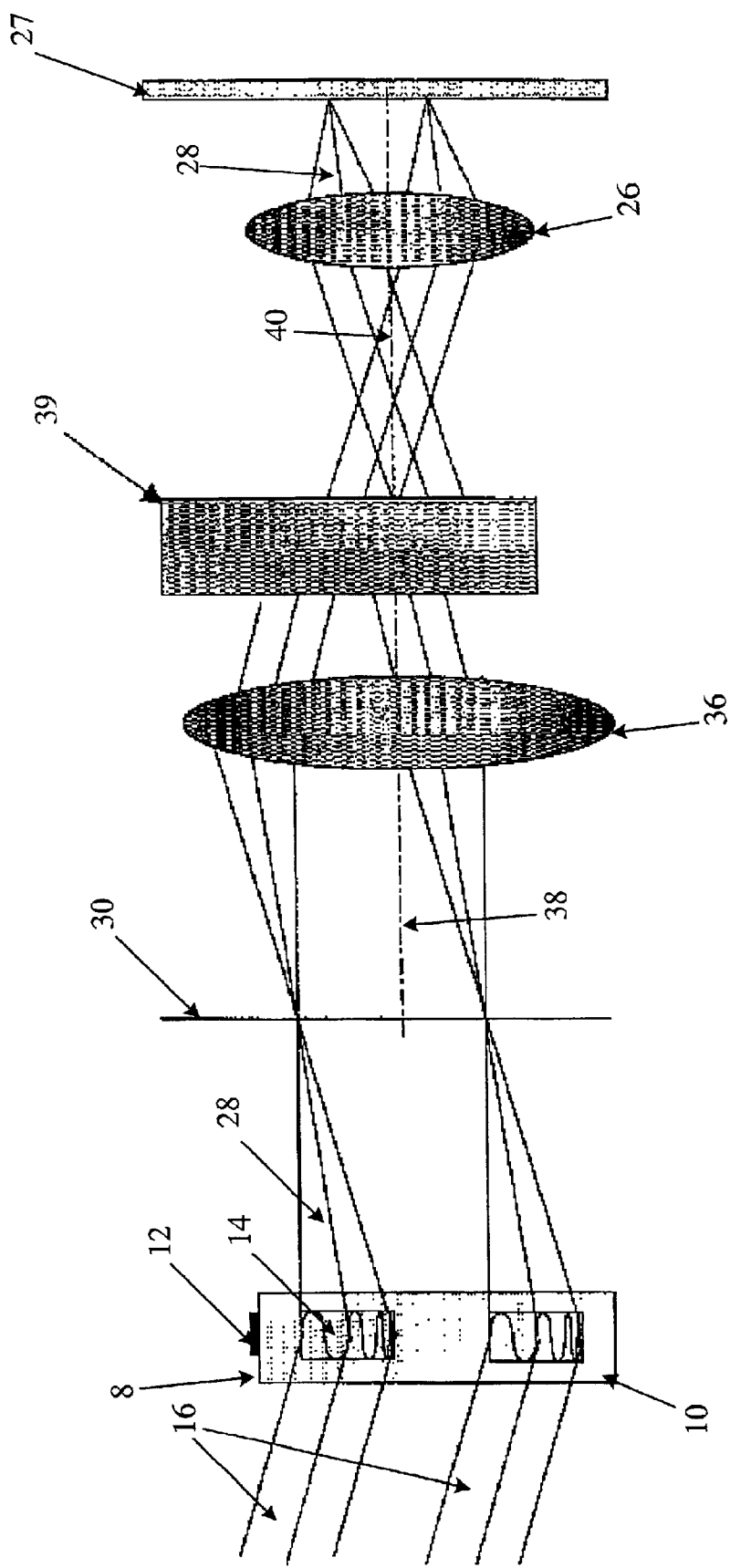
FIG. 2a depicts a schematic of an embodiment of a system that includes an optical mechanism positioned between relay and objective lenses to re-center a pupil of the light collimated by the relay lens onto the objective lens.

In an alternative embodiment, optical axis 38 of relay lens 36 may be centered on scan line 30 produced by AOD 8 as described above. Chief ray 28 produced by AOD 8 may not be substantially parallel to optical axis 38. Optical axis 38 of relay lens 36 may be perpendicular to scan line 30 produced by AOD 8. Relay lens 36 may be configured to collimate light deflected and focused by the AOD and cylinder lens as described in above embodiments. As such, in such an embodiment, light collimated by relay lens 36 may not be centered on objective lens 26. In an additional embodiment shown in FIG. 2*a,* the system may further include optical mechanism 39 such as a prism assembly or system of mirrors positioned between the relay and the objective lenses. The system of mirrors or prism assembly may be configured to re-center a pupil of the light collimated by relay lens 36 onto objective lens 26. Other elements of FIG. 2*a* that may be similarly configured as described with respect to FIG. 2 have been indicated by the same reference numerals.

For systems with a flat field, a spot size on a surface of a specimen may be substantially more uniform across the field than a spot size of systems that do not correct for the field tilt. The sensitivity for laser scanning system may be inversely related to the spot size of the system. If a spot size varies as a function of scan line position, then a sensitivity of the system may also vary as a function of scan line position. As such, a system as described above may have a substantially constant spot size and therefore constant intensity of the beam of light across a length of the focal plane for such a system. Therefore, a system as described herein may have better sensitivity than systems that do not correct for field tilt. In this manner, such a system may also have better system-to-system matching than systems that do not correct for field tilt.

Additionally, correcting for field tilt, for example, by employing de-centered lenses as described herein, may allow utilization of a longer AOD (i.e. an AOD with a longer acoustic propagation distance). Systems that utilize a longer AOD may produce longer scan lines for a given spot size. Increasing a length of scan line for a given spot size may substantially eliminate a need for high precision XY translation stages. Due to the expensive nature of such stages, the cost of a system as described herein may be substantially decreased. Conversely, shorter scan lines may require faster stages, more turns during scanning, and a stage having better vibration isolation. Dynamic straightness requirements for such a stage may also be more difficult to achieve and may require on-the-fly electronic registration.

An AOD operated in chirp mode may have substantial transmission losses due to attenuation of a chirp packet as it propagates through the AOD. The deflection efficiency of a chirp packet decreases as the amplitude of the sound wave decreases, resulting in reduced brightness of the deflected beam as the chirp packet travels through the AOD. Such transmission losses may result in large changes in brightness of a beam as it scans across the surface of the specimen. These brightness variations may reduce system uniformity and may make system-to-system matching difficult.

It is possible to monitor the strength of the acoustic wave in the AOD and to use this monitor signal to normalize detected signals from the specimen. However, this sort of correction only partially compensates for brightness variation across the scan line. The overall sensitivity of the inspection system may still vary with beam brightness, particularly when the detected signal from the specimen is low and photon statistics become important. It is therefore preferable to equalize the actual brightness of the beam as it scans across the specimen.

Figure 3:
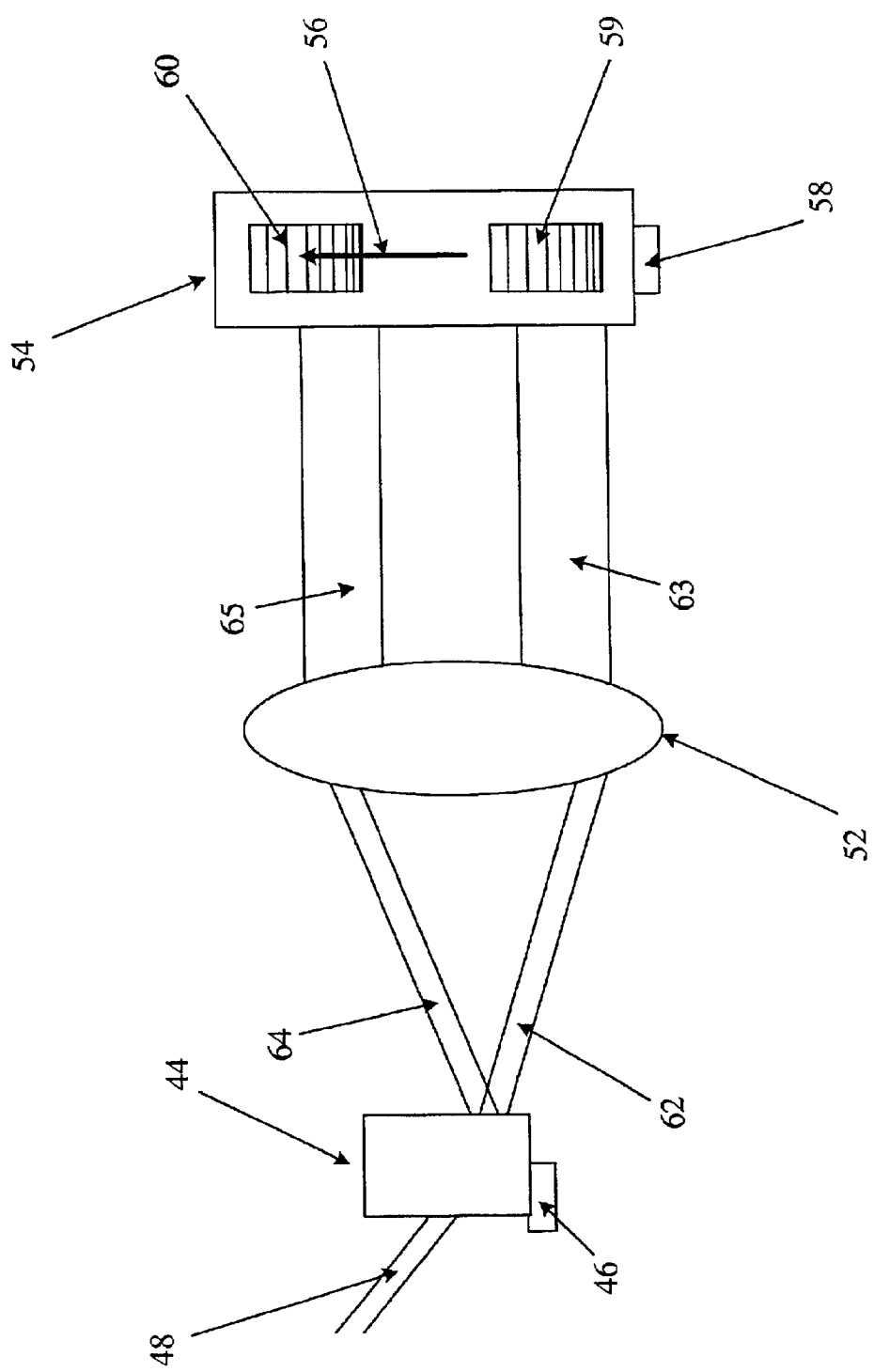
FIG. 3 depicts a schematic of an embodiment of a system that includes a first AOD pre-scanner operated in deflection mode and a second AOD scanner operated in a chirp mode.

An embodiment that may substantially correct for transmission losses associated with a short chirp packet propagating through an AOD is illustrated in FIG. 3. As shown in FIG. 3, a system configured to scan a beam of light over a specimen may include first AOD 44. First AOD 44 may be operated in deflection mode and may be referred to herein as a "prescan" AOD. Transducer 46 attached to AOD 44 may be configured to generate a drive signal which fills AOD 44 with a sound wave whose frequency varies slowly compared to the propagation time of the sound wave through AOD 44. By varying the frequency of the sound wave in AOD 44, the deflected beam may be scanned from location 62 to location 64.

The system may also include lens 52. Lens 52 may be configured to expand the beam and convert the small angular scan from AOD 44 into a long linear scan at AOD 54. The lens may be configured as described in any of the embodiments herein. For example, the lens may include a telescope, a relay lens, a focusing lens, an objective lens, a mirror, or any other appropriate optical component known in the art.

The system may also include second AOD 54. Second AOD 54 may be operated in chirp mode. Transducer 58 attached to AOD 54 may be configured to generate a drive signal which produces a chirp packet which may propagate over a length of AOD 54 from position 59 to position 60. A chirp packet propagating through AOD 54 may be configured to function as a traveling lens to focus the scanning beam. The length of a chirp packet may be approximately equal to the size of light beams 63 and 65, which is much less than the length of second AOD 54.

As chirp packet 59 propagates through second AOD 54 in direction 56 away from transducer 58, the chirp packet may be attenuated in amplitude. Consequently, light focused onto a scan line by a chirp packet at position 54 may be brighter than light focused onto a scan line by a chirp packet at position 60. This non-uniformity in scan line brightness may detrimentally affect the performance of the inspection system or the matching of multiple systems.

In order to compensate for attenuation of a chirp packet as it propagates through second AOD 54, the brightness of the beam illuminating the chirp packet may be varied. This may be accomplished by varying the amplitude of the drive signal applied to first AOD 44 by transducer 46. At the start of the beam sweep, AOD 44 may be driven with a lower amplitude signal, to produce a less bright beam 62 which then illuminates chirp packet 59 near transducer 58 in second AOD 54. At the end of the beam sweep, AOD 44 may be driven with a higher amplitude signal, to produce a brighter beam 64 which then illuminates chirp packet 60 at the end of AOD 54. Amplitude modulation of AOD 44 may thereby compensate for attenuation within AOD 54, producing a final scan line with substantially uniform brightness.

The brightness of a scan line produced by a system as described above may be calibrated by scanning a specimen of uniform reflectivity. Light scattered from different positions along the final scan line may be collected and measured. The amplitude of the drive signal applied to the first AOD may then be modulated as needed to produce a scan line of measured uniform brightness at the specimen. This calibration may compensate not only for attenuation in the second AOD, but for any other non-uniformities in the scanning system.

Figure 4B:
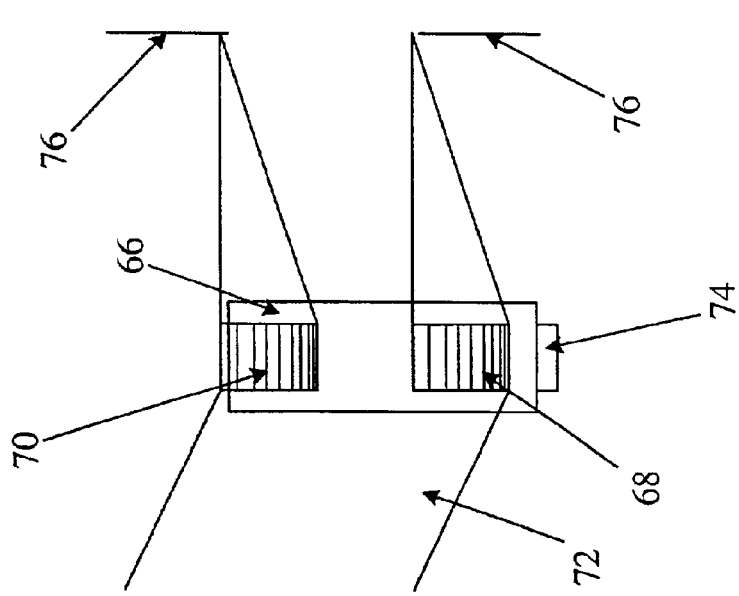
FIGS. 4a and 4b depict schematics of embodiments of a system including a field stop and pre-fill of an AOD in a prescan and flood mode configuration.
Figure 4A:
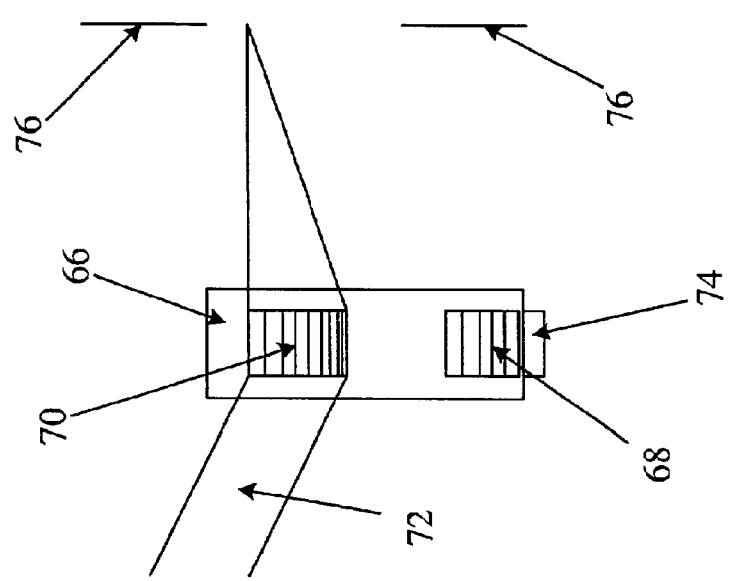

FIGS. 4*a* and 4*b* illustrate embodiments of a system configured to scan a beam of light over a surface of a specimen in multiple sweeps, with little or no delay between the end of one sweep and the start of the next sweep. The system may include AOD 66. AOD 66 may be configured to operate in chirp mode. AOD 66 may contain multiple chirp packets at the same time. Each chirp packet may be substantially shorter than the length of the AOD. For example, AOD 66 may include first chirp packet 68 and second chirp packet 70.

A light source (not shown) may be configured to direct light 72 to illuminate a single chirp packet as it propagates through AOD 66, as illustrated in FIG. 4a. Such a configuration of a light source and AOD may be referred to herein as a "prescan" configuration. An embodiment of such a configuration is illustrated and described previously in FIG. 3.

A light source may alternatively be configured to direct light 72 across substantially an entire length of AOD 66, as illustrated in FIG. 4b. Such a configuration of a light source and AOD may be referred to herein as a "flood mode" configuration. In this manner, light may be directed to first chirp packet 68 and second chirp packet 70 or any number of chirp packets along a length of the AOD substantially simultaneously.

AOD 66 may be coupled to transducer 74. Transducer 74 may be configured to generate a drive signal that may create a chirp packet which may propagate through AOD 66. The chirp packet requires a finite time to form, determined by the desired length of the chirp packet and the acoustic velocity in the AOD. This chirp packet creation time may be referred to herein as a "fill time."

As shown in FIG. 4a, transducer 74 may be used to fill chirp packet 68. After a period of time, this chirp packet may propagate through the AOD to a position such as that indicated by second chirp packet 70. Meanwhile, the transducer may again fill a new chirp packet 68. Both chirp packets may then be propagating through the AOD at the same time. Therefore, both chirp packets may deflect light 72 provided to AOD 66 by a light source operating in a flood mode.

The system may also include field stop 76, located at the focal plane of AOD 66. Field stop 76 may include an aperture, a shutter, a spatial filter or a grating, or any other field stop known in the art. Field stop 76 may be made of a material that may have optical properties such that approximately all of light 72 impinging upon field stop 76 may be absorbed by the field stop. For example, if light 72 includes visible light, the field stop 76 may be made of a substantially opaque material.

The timing of the chirp packets and the size of the field stop may be configured so that light from only one chirp packet at a time may illuminate the specimen. For example, as shown in FIG. 4a, field stop 76 may be configured such that light deflected by second chirp packet 70 may scan the specimen while light deflected by first chirp packet 68 may be blocked. This configuration allows first chirp packet 68 to be filled while the specimen is being scanned with second chirp packet 70. Once chirp packet 68 is filled, it may propagate past the field stop and begin scanning the specimen, just after chirp packet 70 hits the field stop and stops scanning the specimen. Filling one chirp packet while scanning with another chirp packet, as described herein, may be commonly referred to as "pre-filling."

A system employing prefill of a chirp AOD as described herein may substantially continuously scan light over a surface of a specimen, with little or no time delay between consecutive beam sweeps. In the prescan AOD configuration, there may be a delay between sweeps while the prescan AOD is filled, but this fill time can be made shorter than the fill time of a chirp packet in the scanning AOD, resulting in a system with increased throughput.

Further modifications and alternative embodiments of various aspects of the invention may be apparent to those skilled in the art in view of this description. For example, a system configured to scan a beam of light over a surface of a specimen may include de-centered lenses configured to reduce a field tilt of the system, a modulated AOD configured to attenuate an intensity of light provided to a deflection mode AOD, and/or a pre-scanner configured to pre-fill an acoustic cell of a deflection mode AOD. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to scan a beam of light over a surface of a specimen, comprising:
    an acousto-optical deflector configured to focus the beam of light along a scan line; and
    an optical relay system, wherein an optical axis of the relay system is not parallel to a chief ray produced by the acousto-optical deflector at the scan line, and wherein the optical axis of the relay system is substantially perpendicular to a focal plane proximate the surface of the specimen, comprising:
        a relay lens configured to collimate the beam of light from the scan line, wherein an optical axis of the relay lens is substantially centered on the scan line; and
        an objective lens configured to focus the collimated light to the focal plane, wherein an optical axis of the objective lens is substantially de-centered with respect to the optical axis of the relay lens, and wherein the focal plane is substantially parallel to the surface of the specimen.

2. The system of claim 1, wherein a spot size of the beam of light on the surface of the specimen is substantially independent of a position of the beam of light on the surface of the specimen.

3. The system of claim 1, wherein the system is further configured to inspect the surface of the specimen, and wherein a sensitivity of the system is substantially independent of a position of the beam of light on the surface of the specimen.

4. The system of claim 1, wherein the optical axis of the relay lens is substantially perpendicular to the scan line, and wherein the optical axis of the relay lens is not parallel to the chief ray.

5. The system of claim 1, wherein the optical axis of the objective lens is substantially perpendicular to the focal plane.

6. The system of claim 1, wherein the collimated light is substantially centered on the objective lens.

7. The system of claim 1, wherein the optical axis of the objective lens is substantially centered on the focal plane.

8. The system of claim 1, wherein the acousto-optical deflector has a bandwidth of less than or equal to approximately 1 octave.

9. The system of claim 1, wherein a length of a chirp packet in the acousto-optical deflector is shorter than a length of the acousto-optical deflector.

10. The system of claim 1, further comprising an optical mechanism located between the relay and objective lenses, wherein the optical mechanism is configured to re-center the collimated light from the relay lens onto the objective lens.

11. A method for scanning a beam of light over a surface of a specimen, comprising:
focusing the beam of light along a scan line with an acousto-optical deflector; and
relaying the scan line to a focal plane proximate the surface of the specimen with an optical relay system, wherein an optical axis of the relay system is not parallel to a chief ray produced by the acousto-optical deflector at the scan line, and wherein the optical axis of the relay system is substantially perpendicular to the focal plane, comprising:
collimating the light from the scan line with a relay lens, wherein an optical axis of the relay lens is substantially centered on the scan line; and
focusing the collimated light to the focal plane with an objective lens, wherein an optical axis of the objective lens is substantially de-centered with respect to the optical axis of the relay lens, and wherein the focal plane is substantially parallel to the surface of the specimen.

12. The method of claim 11, wherein a spot size of the beam of light on the surface of the specimen is substantially independent of a position of the beam of light on the surface of the specimen.

13. The method of claim 11, further comprising inspecting the surface of the specimen, wherein a sensitivity of inspection is substantially independent of a position of the beam of light on the surface of the specimen.

14. The method of claim 11, wherein the optical axis of the relay lens is substantially perpendicular to the scan line, and wherein the optical axis of the relay lens is not parallel to the chief ray.

15. The method of claim 11, wherein the optical axis of the objective lens is substantially perpendicular to the focal plane.

16. The method of claim 11, wherein the collimated light is substantially centered on the objective lens.

17. The method of claim 11, wherein the optical axis of the objective lens is substantially centered on the focal plane.

18. The method of claim 11, wherein the acousto-optical deflector has a bandwidth of less than or equal to approximately 1 octave.

19. The method of claim 11, wherein a length of a chirp packet in the acousto-optical deflector is shorter than a length of the acousto-optical deflector.

20. The method of claim 11, further comprising re-centering the collimated light onto the objective lens with an optical mechanism located between the relay lens and objective lens.

21. A system configured to scan a beam of light over a surface of a specimen, comprising:
a first acousto-optical deflector configured to direct the beam of light at various angles along an angular scan, wherein an amplitude of the first acousto-optical deflector is modulated such that an intensity of the directed light varies over a length of the angular scan;
a lens configured to expand the directed beam of light and to convert the angular scan to linear scan; and
a second acousto-optical deflector configured as a traveling lens to focus the beam of light onto a scan line.

22. The system of claim 21, wherein the intensity of the light increases over the scan line of the first acousto-optical deflector as transmission losses increase over the length of the second acousto-optical deflector.

23. The system of claim 21, wherein an intensity of the light directed by the second acousto-optical deflector is substantially independent of a position of the directed beam of light on the surface of the specimen.

24. The system of claim 21, wherein the system is further configured to inspect the surface of the specimen, and wherein a sensitivity of the system is substantially independent of a position of the directed beam of light on the surface of the specimen.

25. The system of claim 21, wherein the first acousto-optical deflector is calibrated with a substantially uniform scattering feature.

26. The system of claim 21, wherein a duration of a drive signal of the first acousto-optical deflector is greater than a time required for a chirp packet to propagate across the beam of light.

27. The system of claim 21, wherein a duration of a drive signal time of the second acousto-optical deflector is less than a time required for a chirp packet to propagate across the second acousto-optical deflector.

28. A method for scanning a beam of light over a surface of a specimen, comprising:
directing the beam of light at various angles along an angular scan with a first acousto-optical deflector, wherein an amplitude of the first acousto-optical deflector is modulated such that an intensity of the directed light varies over a length of the angular scan;
expanding the directed beam and converting the angular scan into a linear scan with a lens; and
focusing the expanded beam to a scan line with a second acousto-optical deflector configured as a traveling lens.

29. The method of claim 28, wherein the intensity of the light increases over the scan line of the first acousto-optical deflector as transmission losses increase over the length of the second acousto-optical deflector.

30. The method of claim 28, wherein an intensity of the light deflected by the second acousto-optical deflector is substantially independent of a position of the directed beam of light on the surface of the specimen.

31. The method of claim 28, further comprising inspecting the surface of the specimen, wherein a sensitivity of inspection is substantially independent of a position of the directed beam of light on the surface of the specimen.

32. The method of claim 28, further comprising calibrating the first acousto-optical deflector with a substantially uniform scattering feature.

33. The method of claim 28, wherein a duration of a drive signal of the first acousto-optical deflector is greater than a time required for a chirp packet to propagate across the beam of light.

34. The method of claim 28, wherein a duration of a drive signal time of the second acousto-optical deflector is less than a time required for a chirp packet to propagate across the second acousto-optical deflector.

35. A system configured to scan a beam of light over a surface of a specimen, comprising an acousto-optical deflector comprising at least a first chirp packet and a second chirp packet, wherein the first chirp packet can be filled with an acoustic signal while the second chirp packet propagates through the acousto-optical deflector and focuses the beam of light onto a scan line.

36. The system of claim 35, wherein the system is further configured to inspect the surface of the specimen, and wherein an average data rate of the system is approximately equal to a peak data rate of the system.

37. The system of claim 35, further comprising a field stop configured to allow light from the second chirp packet to scan the surface of the specimen while blocking light from the first chirp packet.

38. The system of claim 35, further comprising a pre-scanner acousto-optical deflector configured to direct the beam of light to the first or the second chirp packet.

39. A method for scanning a beam of light over a surface of a specimen, comprising filling a first chirp packet of an acousto-optical deflector with an acoustic signal while focusing the beam of light onto a scan line with a second chirp packet propagating through the acousto-optical deflector.

40. The method of claim 39, further comprising inspecting the surface of the specimen, wherein an average data rate of inspection is approximately equal to a peak data rate of inspection.

41. The method of claim 39, further comprising allowing light from the second chirp packet to scan the surface of the specimen with a field stop and blocking light from the first chirp packet with the field stop.

42. The system of claim 39, further comprising directing the beam of light to the first or second chirp packet with a pre-scanner acousto-optical deflector.

* * * * *